US010327754B2

(12) United States Patent
Denham

(10) Patent No.: US 10,327,754 B2
(45) Date of Patent: Jun. 25, 2019

(54) KNOTLESS SUTURE ANCHOR

(71) Applicant: Biomet Sports Medicine, LLC, Warsaw, IN (US)

(72) Inventor: Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 214 days.

(21) Appl. No.: 15/134,002

(22) Filed: Apr. 20, 2016

(65) Prior Publication Data

US 2016/0310128 A1 Oct. 27, 2016

Related U.S. Application Data

(60) Provisional application No. 62/152,306, filed on Apr. 24, 2015.

(51) Int. Cl.
*A61B 17/16* (2006.01)
*A61B 17/00* (2006.01)
*A61B 17/04* (2006.01)

(52) U.S. Cl.
CPC ...... *A61B 17/0401* (2013.01); *A61B 17/1604* (2013.01); *A61B 2017/00349* (2013.01);
(Continued)

(58) Field of Classification Search
CPC ........ A61B 17/0401; A61B 2017/0409; A61B 2017/0412; A61B 2017/0414; A61B 2017/042; A61B 2017/0422; A61B 2017/0424; A61B 2017/0425; A61B 2017/0427; A61B 2017/0429; A61B 2017/043; A61B 2017/0432;
(Continued)

(56) References Cited

U.S. PATENT DOCUMENTS 5,849,004 A * 12/1998 Bramlet ............. A61B 17/0401
606/232
6,146,407 A * 11/2000 Krebs ................ A61B 17/0401
606/104
(Continued)

OTHER PUBLICATIONS

"Linvatec Shoulder Restoration System", [Online]. Retrieved from the Internet: <URL: http://www.endoprotez.com/pdf/CBR3045_PopLok.pdf, (2009), 2 pgs.
(Continued)

*Primary Examiner* — Martin T Ton
(74) *Attorney, Agent, or Firm* — Schwegman Lundberg & Woessner, P.A.

(57) ABSTRACT

Methods, systems and apparatuses for soft tissue repair including a device for anchoring sutured tissue to a bone are disclosed. According to one example, the device can include a body and a member. The body can have a wall with an outer surface thereof configured to engage the bone of a patient. The body can define an inner passage extending generally from a proximal end thereof to a distal end thereof. The wall can have a first side having a first size that differs from a second size of a second side of the wall. The member can be configured to be disposed within the body and can be moveable along the inner passage relative to the body between a first position and a second position. The member can be configured with an eyelet to receive and pass a suture through the member when the member is in the first position.

18 Claims, 10 Drawing Sheets

(52) U.S. Cl.
CPC .......... *A61B 2017/0409* (2013.01); *A61B 2017/0412* (2013.01); *A61B 2017/0414* (2013.01); *A61B 2017/0445* (2013.01); *A61B 2017/0451* (2013.01)

(58) Field of Classification Search
CPC .... A61B 2017/0433; A61B 2017/0435; A61B 2017/0437; A61B 2017/0438; A61B 2017/0445; A61B 2017/0403; A61B 2017/0454; A61B 2017/0458; A61F 2/0811; A61F 2002/0817; A61F 2002/0823; A61F 2002/0829; A61F 2002/0835; A61F 2002/0841
USPC ......................................................... 606/232
See application file for complete search history.

(56) References Cited

U.S. PATENT DOCUMENTS

| | | | |
|---|---|---|---|
| 8,221,433 B2 | 7/2012 | Lozier | |
| 2012/0078298 A1* | 3/2012 | Sklar | A61B 17/0401 606/232 |
| 2013/0267998 A1* | 10/2013 | Vijay | A61B 17/0401 606/232 |
| 2017/0119367 A1 | 5/2017 | Denham | |

OTHER PUBLICATIONS

"U.S. Appl. No. 15/338,945, Restriction Requirement dated Nov. 28, 2018", 5 pgs.
"U.S. Appl. No. 15/338,945, Response filed Jan. 16, 2019 to Restriction Requirement dated Nov. 28, 2018", 9 pgs.

* cited by examiner

KNOTLESS SUTURE ANCHOR

CLAIM OF PRIORITY

This application claims the benefit of U.S. Provisional Patent Application Ser. No. 62/152,306, filed on Apr. 24, 2015, the benefit of priority of which is claimed hereby, and which is incorporated by reference herein in its entirety.

FIELD

The present subject matter relates to surgical procedures and devices and, more particularly, to prostheses, systems and methods related to soft tissue repair.

BACKGROUND

The successful reattachment of soft tissue to bone can be a significant concern, especially in the sports medicine industry.

The majority of soft tissue repairs involve suture anchors or tacks. In such methods, an anchor or tack is readied for insertion into bone and a suture is passed through tissue and the anchor or tack and knotted or otherwise connected thereto. While holding tension on the suture, joint stability is evaluated and the anchor or tack is deployed into the bone, finalizing the repair.

OVERVIEW

This disclosure pertains generally to systems, methods and devices that facilitate the rapid connection of sutures to tissue fixation implants such as a suture anchor. The disclosure also pertains to systems, methods and devices that facilitate the rapid implantation and firm fixation of the suture anchor in bone. For example, the systems, methods and devices can facilitate the passage of one or more sutures through the suture anchor and the connection of the one or more sutures to the suture anchor with a minimal change in tension on the one or more sutures from prior to and after deployment of the suture anchor into bone. In some examples, the fixation of the suture anchor into bone can be accomplished by the geometry of the suture anchor which allows for fixation of the suture anchor in the bone by simply rotating the suture anchor about its longitudinal axis. Deployment of the suture anchor into bone can be accomplished with rapid fixation technology (RFT), which provides the ability to rapidly and precisely deliver the suture anchor to a desired location.

The present inventor has recognized, among other things, that existing soft tissue fixation solutions can require a multiple step process where connection of the suture to the suture anchor can be challenging and time consuming. This process can include deploying an anchor into bone and connecting suture(s) to the deployed anchor. It can often be difficult to accomplish such connection as the suture(s) must be knotted or otherwise connected while maintaining the suture at a desired amount of tension. Failure to provide adequate tension (providing too much or too little) can cause the suture(s) to be ineffective necessitating repetition of the entire process in some cases.

Considering these factors, the present inventor proposes an anchoring device and related systems and methods that can reduce the number of currently used surgical processes to provide for faster, easier, and more reproducible surgical techniques. Thus, the present application discloses an anchor device configuration where upon deployment of the anchor device, connection of the suture(s) to the anchor is accomplished and a desired tension is substantially maintained during this process. In some examples, the suture anchor can be configured to be affixed into the bone by simply rotating the suture anchor about its longitudinal axis, thereby reducing the number of additional steps required during the surgical process.

To further illustrate the apparatuses, systems and methods disclosed herein, the following non-limiting examples are provided:

Example 1 is a device for anchoring sutured tissue to a bone, the device can comprise: a body having a wall with an outer surface thereof configured to engage a bone of a patient, the body defining an inner passage extending generally from a proximal end thereof to a distal end thereof, the wall having a first side having a first size that differs from a second size of a second side of the wall; and a member configured to be disposed within the body and moveable along the inner passage relative to the body between a first position and a second position, wherein the member is configured with an eyelet to receive and pass a suture through the member when the member is in the first position.

In Example 2, the subject matter of Example 1 optionally includes wherein the body has an irregular cross-sectional profile along a longitudinal axis from the proximal end to the distal end of the body such that at least the first side varies in shape with a differing thickness along the longitudinal axis.

In Example 3, the subject matter of any one or more of Examples 1-2 optionally include wherein the first side of the wall includes one or more projections and one or more valleys along at least a part of the outer surface thereof, the one or more projections and the one or more valleys extending along the longitudinal axis.

In Example 4, the subject matter of Example 3 optionally includes wherein the wall includes at least a third side with one or more projections and one or more valleys along at least a second part of the outer surface thereof, the third side spaced at an angle from the first side about the longitudinal axis.

In Example 5, the subject matter of any one or more of Examples 3-4 optionally include wherein the wall includes at least a third side with one or more projections and one or more valleys along at least a second part of the outer surface thereof, the third side spaced at substantially 180 degrees from the first side about the longitudinal axis.

In Example 6, the subject matter of Example 5 optionally includes wherein the wall includes at least a fourth side spaced 180 degrees from the second side about the longitudinal axis, and wherein a first distance between the outer surface of the second side of the wall and the outer surface of the fourth side of the wall is less than a second distance between the outer surface of the third side of the wall and the outer surface of the first side of the wall.

In Example 7, the subject matter of any one or more of Examples 1-6 optionally include wherein the first side has a first thickness in cross-section and the second side having a second thickness in cross-section, and wherein the first thickness differs from the second thickness, and wherein the first side is disposed transverse to the second side and the first thickness exceeds the second thickness.

In Example 8, the subject matter of any one or more of Examples 1-7 optionally include wherein the member comprises: a bullet having a distal end configured to engage the bone of the patient, the bullet configured to remain within the body; and a deployment pin configured to be detachable from the bullet and removable from the body, wherein the deployment pin is actuateable relative to the body to move the bullet to the second position relative to the body and thereby form a deployed configuration of the device.

In Example 9, the subject matter of Example 8 optionally includes wherein the deployment pin forms the eyelet and the deployment pin is configured to pull the suture through the inner passage and out of the proximal end of the body.

In Example 10, the subject matter of any one or more of Examples 1-9 optionally include wherein the body comprises an expandable shell with deformable wing projections along at least the first side and has a slit formed by the wall thereof, the slit extending at least a portion of a proximal-distal length of the wall, and wherein the member has a protrusion from an outer surface thereof that generally aligns with the proximal-distal extending slit, the member is configured to facilitate expansion of the body when the member is in the second position relative to the first position.

Example 11 is a system for anchoring a sutured tissue to a bone, the system can comprise: one or more sutures; an outer body having a wall with an outer surface configured to engage a bone of a patient, the body having an inner passage extending generally from a proximal end thereof to a distal end thereof; an inner bullet configured to be disposed within the body and moveable along the inner passage relative to the body between a first position and a second position, wherein with movement of the bullet toward the second position the one or more sutures move proximally from at least one of the first and second apertures toward the proximal end of the body; and a surgical tool configured to actuate movement of the bullet relative to the body between the first position and the second position via a deployment pin that is coupleable to the bullet, the deployment pin configured to be detachable from the bullet and removable from the body.

In Example 12, the subject matter of Example 11 optionally includes wherein the body has an irregular cross-sectional profile along a longitudinal axis from the proximal end to the distal end of the body such that at least a first thickness of a first side of the wall varies along the longitudinal axis.

In Example 13, the subject matter of any one or more of Examples 11-12 optionally include wherein the wall has a first side with a first thickness in cross-section and the wall has a second side with a second thickness in cross-section, and wherein the first thickness differs from the second thickness.

In Example 14, the subject matter of Example 13 optionally includes wherein the first side of the wall includes one or more projections and one or more valleys along at least a part of the outer surface thereof, the one or more projections and the one or more valleys extending along a longitudinal axis of the body.

In Example 15, the subject matter of any one or more of Examples 13-14 optionally include wherein the wall includes at least a third side with one or more projections and one or more valleys along at least a second part of the outer surface thereof, the third side spaced at an angle from the first side about a longitudinal axis of the body.

In Example 16, the subject matter of any one or more of Examples 13-15 optionally include wherein the wall includes at least a third side spaced 180 degrees from the first side about a longitudinal axis and a fourth side spaced 180 degrees from the second side about the longitudinal axis, and wherein a first distance between the outer surface of the second side of the wall and the outer surface of the fourth side of the wall is less than a second distance between the outer surface of a third side of the wall and the outer surface of the fourth side of the wall.

In Example 17, the subject matter of any one or more of Examples 11-16 optionally include a tap tool having one or more cutting edges configured to cut cancellous bone, the tap tool having a cross-sectional profile configured to substantially match a cross-sectional profile of the body and the bullet with the bullet in the first position.

Example 18 is a method of deploying a suture anchor into bone, the method can comprise: inserting a tap tool into the bone to create a first recess in the bone; rotating the tap tool about a longitudinal axis to create a second recess in the bone; inserting the suture anchor into the first recess, the suture anchor comprising an outer body having a wall with an outer surface configured to engage the bone of a patient and an inner bullet configured to be disposed within the body and moveable along the inner passage relative to the body between a first position and a second position; rotating the suture anchor into the second recess in the bone; and actuating movement of the bullet relative to the body between the first position and the second position.

In Example 19, the subject matter of Example 18 optionally includes detaching an actuation device from the bullet and removing the actuation device from the body.

In Example 20, the subject matter of any one or more of Examples 18-19 optionally include wherein the wall has a first side with a first thickness in cross-section and the wall has a second side with a second thickness in cross-section, and wherein the first thickness differs from the second thickness.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to systems, methods and devices that facilitate the rapid connection of sutures to tissue fixation implants such as a suture anchor. For example, the systems, methods and devices can facilitate the passage of one or more sutures through the suture anchor and the connection of the one or more sutures to the suture anchor with a minimal change in tension on the one or more sutures from prior to and after deployment of the suture anchor into bone. In some examples, a fixation of the suture anchor into bone can be accomplished by the geometry of the suture anchor, which allows for fixation of the suture anchor in the bone by simply rotating the suture anchor about its longitudinal axis. The present systems, methods and devices can be used in conjunction with one or more bone fixation tools (also referred to a "deployment devices" "deployment tool" "actuation tools" "actuation devices" or simply as a "surgical tool" herein) such as the one as disclosed in U.S. Provisional Patent Application Ser. No. 62/250,719, filed Nov. 4, 2015, and U.S. Pat. No. 8,221,433, which are both incorporated by reference in their entirety. The methods and devices described herein can use a modified tool similar to that disclosed in the '433 patent. The present tissue fixation implants have applicability to a variety of orthopedic procedures as well as to the sports medicine industry. Thus, the present implants are applicable to the repair of and/or fixation to various anatomical locations and features including, for example, the labrum of the shoulders and hips.

Figure 1:
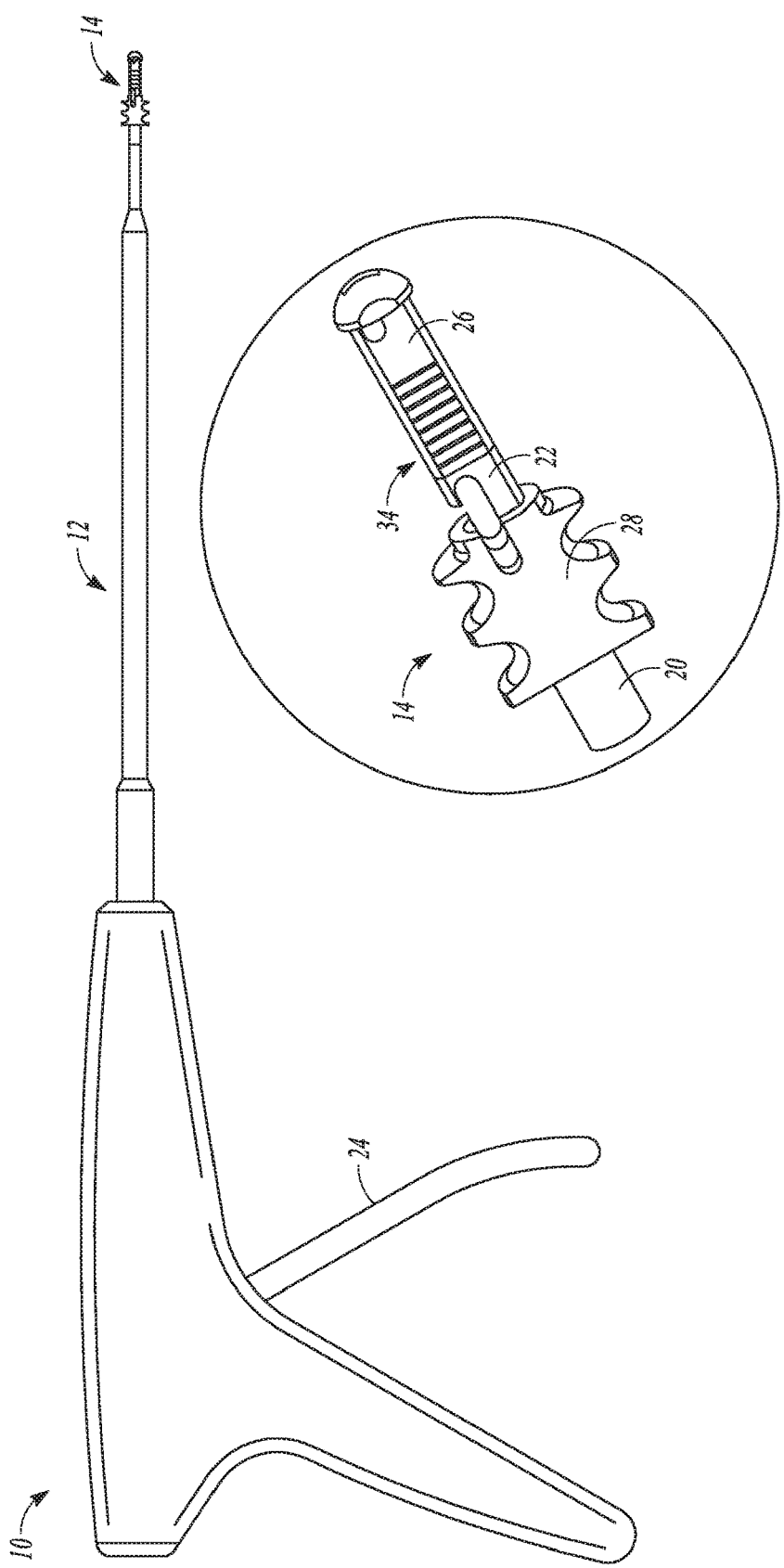
FIG. 1 illustrates a system for soft tissue repair including an anchoring device in accordance with an example of the present application.
Figure 2:
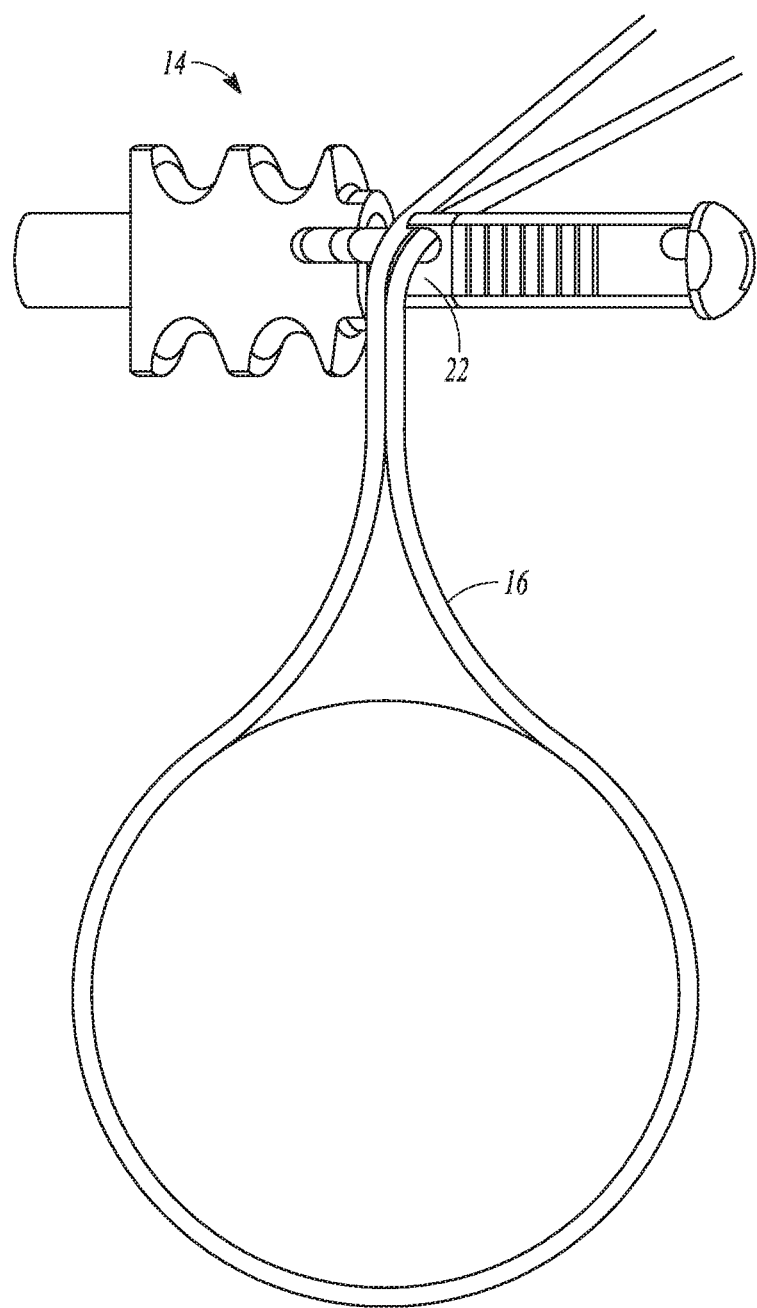
FIG. 2 shows the system of FIG. 1 further including a suture passed around tissue and through an actuating tool of the system in accordance with an example of the present application.

FIG. 1 shows a system 10 for repair of soft tissue. The system 10 includes a deployment tool 12, an anchoring device 14, and one or more sutures 16 (FIG. 2). In some examples, a threading tool (not shown) can be used with the system 10 in the manner discussed in the '719 application. However, the system 10 need not employ the threading tool in all examples.

The deployment tool 12 can be configured for facilitating fixation of the anchoring device 14 into bone of a patient. As such, the deployment tool 12 can comprise a tool similar to that disclosed in the '433 patent and the '719 application. As is shown in the enlargement of the distal portion of the deployment tool 12 in FIG. 1, the deployment tool 12 can have an outer cannula 20, an inner shaft (not shown) residing inside and movable relative to the outer cannula 20, and a pin 22 coupled to and extending from a distal end of the inner shaft.

Movement of the inner shaft relative to the outer cannula 20 can be facilitated by a trigger 24. The pin 22 can be configured to couple with the anchoring device 14 and actuate one portion (an inner bullet 26) of the anchoring device 14 relative to another portion (an outer body 28) in a manner to be discussed subsequently. The enlarged view of the distal portion of the deployment tool 12 in FIG. 1 provides examples of the inner bullet 26, the pin 22 and the outer body 28 in a non-deployed first position. As used herein, the inner bullet 26 and the pin 22 can be referred to as an inner member 34 or simply as a member herein.

FIG. 2 shows the one or more sutures 16 passing through the anchoring device 14 (and more particularly an eyelet of the pin 22) in further detail. The suture(s) 16 can comprise any type currently known, and thus, can be constructed of various materials and can be monofilament and/or multifilament as desired, for example. If used the threading tool can be configured to couple to the outer cannula 20 or another portion of the deployment device 12. The threading tool can additionally include a loop constructed of a flexible material such as fiber. The loop can be configured for insertion through the eyelet of the pin 22 of the deployment tool 12. More particularly, the loop can be configured to receive the one or more sutures 16 and can fit through the eyelet of the pin 22 to draw the suture(s) 16 therethrough. As is illustrated in FIG. 2, the suture(s) 16 can be drawn through the pin 22 prior to deployment of the anchoring device 14 into bone. Once the suture(s) 16 has been drawn through the pin 22, the threading tool can be removed from the deployment tool 12.

Figure 3A:
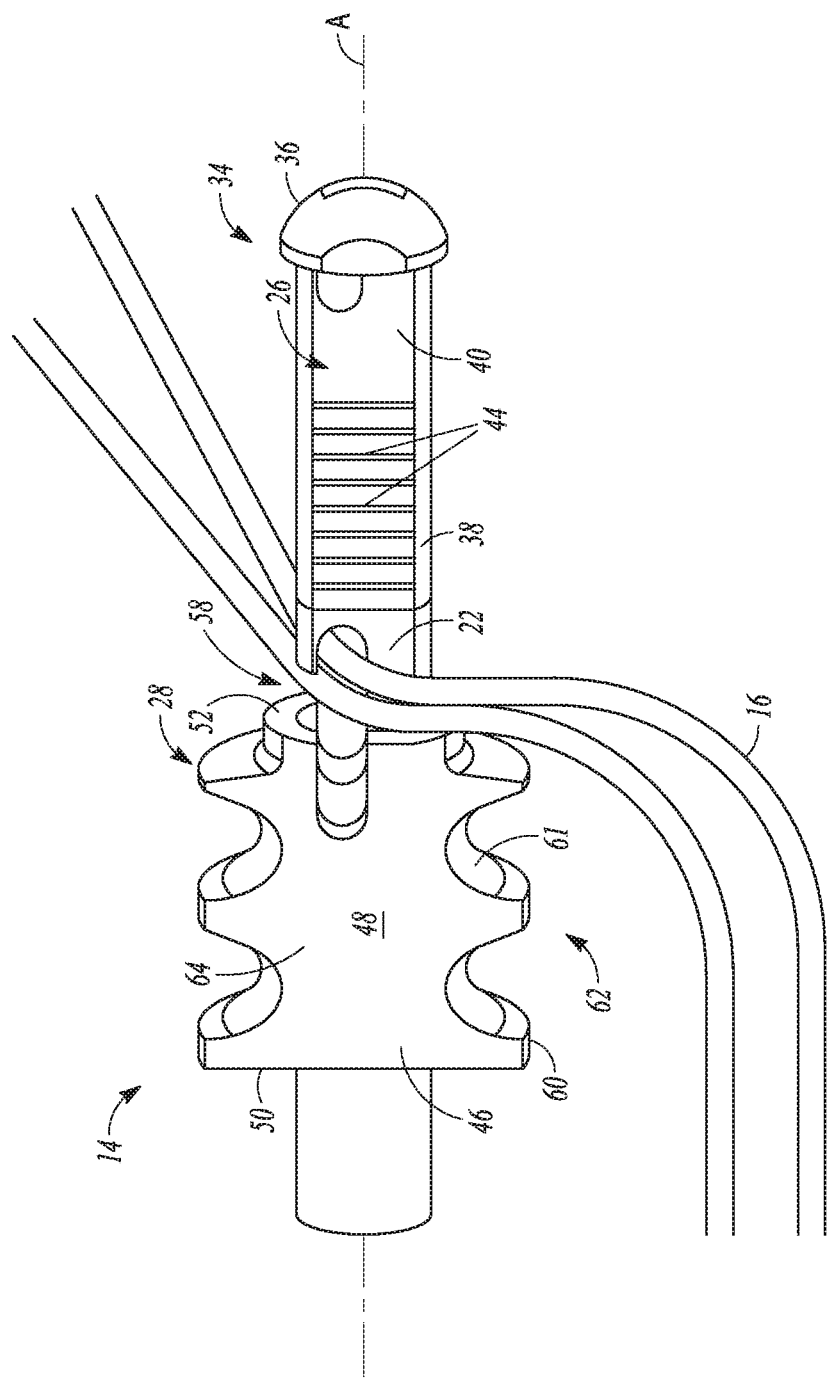
FIG. 3A shows a view of the anchoring device in a non-deployed position from a first perspective in accordance with an example of the present application.
Figure 3B:
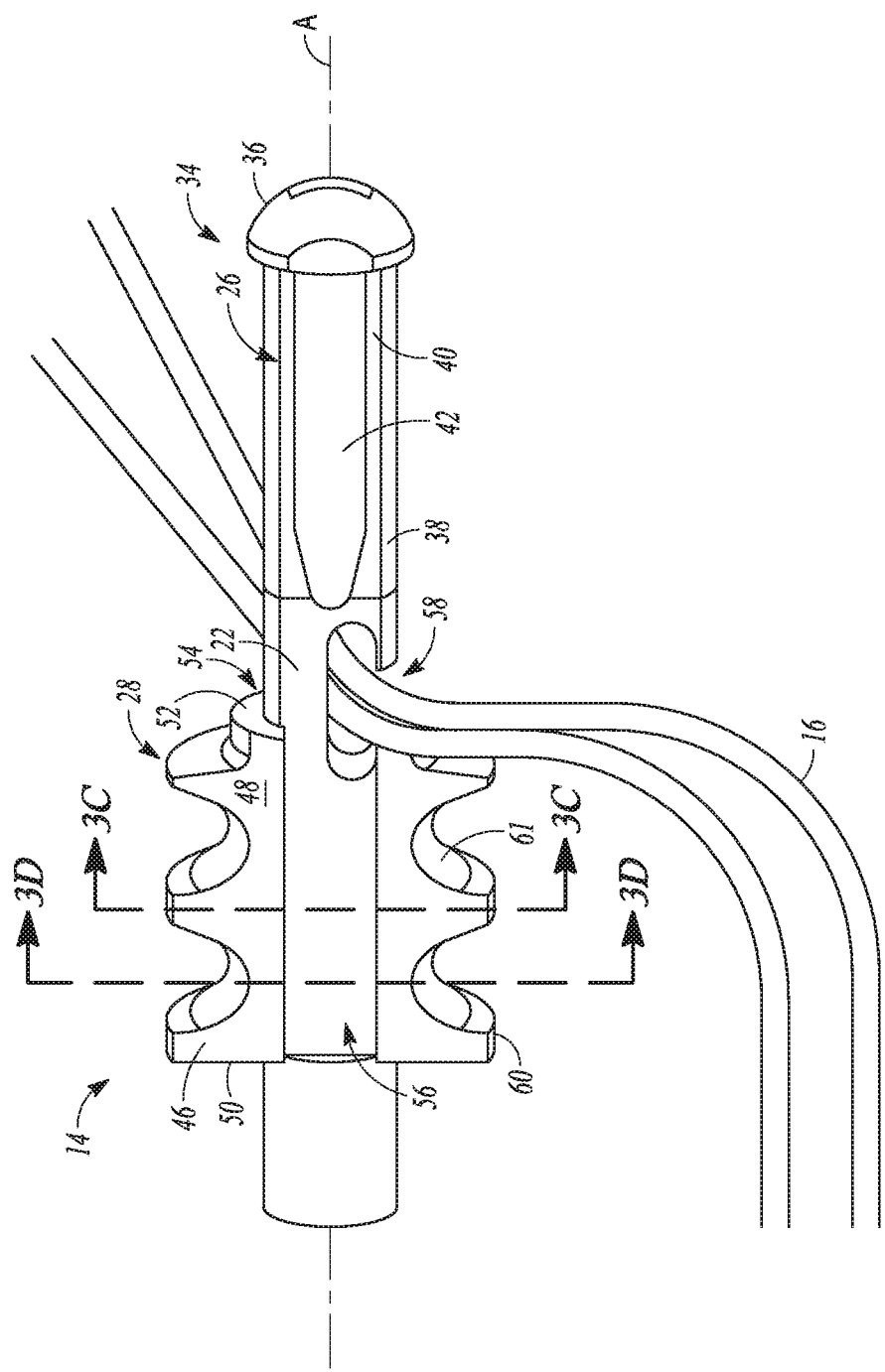
FIG. 3B shows a view of the anchoring device in the non-deployed position from a second perspective in accordance with an example of the present application.
Figure 3C:
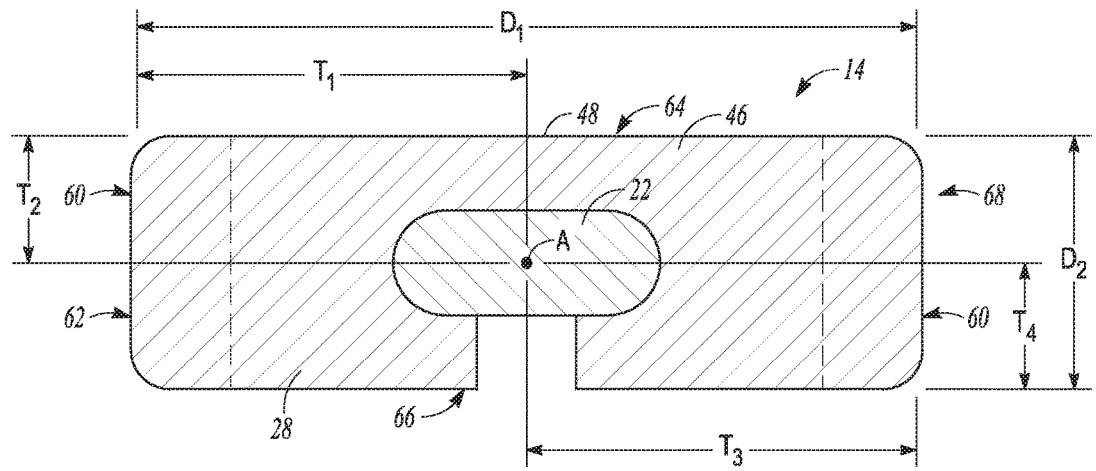
FIGS. 3C and 3D are cross-sections of the anchoring device and the actuation tool taken along the lines shown in FIG. 3B.
Figure 3D:
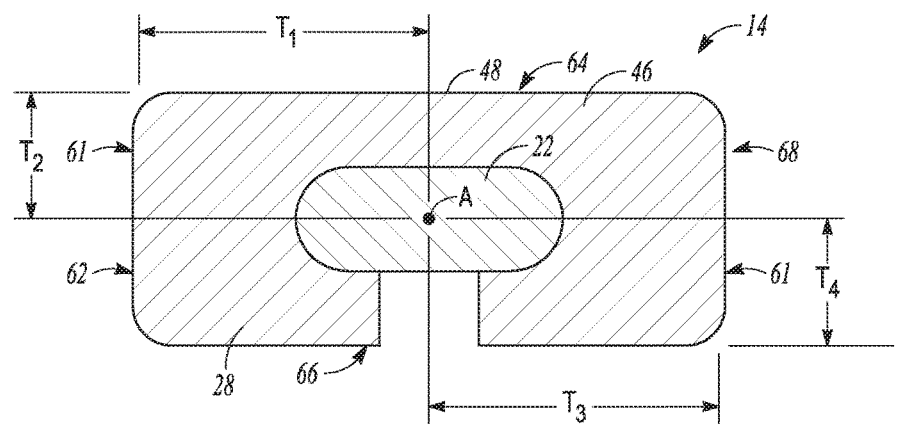

FIGS. 3A to 3D show views of the anchoring device 14 and the pin 22 from various perspectives including in cross-section in FIGS. 3C and 3D. As discussed previously, the anchoring device 14 can be comprised of the inner bullet 26 and outer body 28 and can have an elongate shape extending along longitudinal axis A. Collectively the inner bullet 26 and the pin 22 can comprise the inner member 34 that is configured to be received in and is moveable relative to the outer body 28 in the manner discussed subsequently.

According to the example of FIGS. 3A and 3B, the inner bullet 26 can include a distal end portion 36, a proximal end portion 38, a body 40, a protrusion 42 (FIG. 3B), and a textured portion 44 (FIG. 3A). The outer body 28 can include a wall 46 having an outer surface 48, a proximal end portion 50, a distal end portion 52, an inner passage 54 (FIG. 3B), and a slit 56 (FIG. 3B). The pin 22 can include an eyelet 58.

As is generally shown in FIGS. 3A and 3B the inner bullet 26 is disposed in a first (non-deployed) position relative to the outer body 28. The inner bullet 26 and the outer body 28 can be configured to couple together in a manner that allows the inner bullet 26 to translate proximally relative to outer body 28 into a second (deployed) position where the inner bullet 26 is received within the outer body 28 (example shown in FIG. 4). More particularly, the pin 22 can be actuateable relative to the outer body 28 to move the inner bullet 26 to the second position relative to the outer body 28 and can thereby form a deployed configuration of the anchoring device 14. The pin 22 can have the eyelet 58 therethrough. The eyelet 58 can have an opening configured to facilitate reception of the suture 16 within the eyelet as shown in FIGS. 3A and 3B. The pin 22 can be configured to be detachable from the inner bullet 26 (e.g., by unscrewing, unhooking, breaking, unsnapping, or the like) and can be configured to be removable from the outer body 28 according to some examples.

The distal end portion 36 of the bullet 26 can be configured as a blunt, sharp and/or expanded tip that is configured to engage with bone of the patient. The bullet 26 can have a somewhat rectangular cross-sectional shape with tapered corners from adjacent the distal end portion 36 to the opposing proximal end portion 38 according to the examples shown in FIGS. 3A and 3B. The bullet 26 can be shaped and sized to be received and substantially fill the inner passage 54 while still allowing for locking passage of the suture 16 through the inner passage 54 according to some examples.

The body 40 can extend along the longitudinal axis A and can have sides of differing configuration as will be discussed subsequently in reference to FIGS. 3C and 3D. The body 40 can connect the distal end portion 36 to the proximal end portion 38. The protrusion 42 (FIG. 3B) can extend outward from an outer surface of the body 40, and thus, can increase the extent thereof. According to some examples the protrusion 42 can include a keel and/or a textured surface along an outer extent thereof. However, such features are not shown in the example of FIG. 3B. The textured portion 44 (FIG. 3A) can be arranged on a generally opposing side of the body 40 from the protrusion 42.

As shown in the example of FIG. 3B, the protrusion 42 can generally align with the proximal-distal extending slit 56 formed by the wall 46 when the member 34 is in the first position. The textured portion 44 can be substantially flat as shown in FIG. 3A. The textured portion 44 can be configured to engage the suture 16 as shown in FIG. 3A and generally maintain a position of the suture relative to the member 34 as the member 34 moves from the first position (FIGS. 3A and 3B) to the second position (FIG. 4) relative to the outer body 28. According to the illustrated example, the textured portion 44 can be recessed relative to a remainder of an outer surface (e.g. outer surface of body 40) of the member 34 and the recess can facilitate passage of a suture between the member 34 and the outer body 28 as the member 34 moves from the first position to the second position relative to the outer body 28.

Turning to the outer body 28, the wall 46 can separate the generally opposing inner surface from the outer surface 48. The outer surface 48 can have wing projections 60 and troughs 61 on a first side 62 and can have a second side 64 that differs in shape and/or size from the first side 62 according to the example of FIG. 3A. According to other examples, the outer surface 48 can be textured or otherwise configured to engage the bone of a patient. Features such as the wing projections 60 and troughs 61 can facilitate engagement with the bone to fix the anchoring device 14 within the bone as discussed subsequently.

The wall 46 can extend along the longitudinal axis A from the proximal end portion 50 to the distal end portion 52 and can define the inner passage 54. In some cases, the wall 46 may not extend entirely around and entirely form the inner passage 54 but can be split along the slit 56 (FIG. 3B). The slit 56 can extend at least a portion of a proximal-distal length of the wall 46 from the proximal end portion 50 to the distal end portion 52. The extent of slit 56 can initially be less than an entire proximal-distal length of the wall 46 (i.e. a distal portion of the wall 46 may entirely surround the inner passage 54). However, in some cases slit 56 can be configured to grow to the entire proximal-distal length of the wall 46 upon deployment of the bullet 26. Thus, deployment of the bullet 26 can tear the wall 46 and increase the size of the slit 56.

The inner passage 54 can extend generally from the proximal end portion 50 to the distal end portion 52 along the longitudinal axis A. The pin 22 (and inner member 34) can be configured to pass through the outer body 28 via the inner passage 54. However, the bullet 26 can be configured to obstruct communication through the inner passage 54 (e.g. grasp and hold the suture 16 in place) when the bullet 26 is in the second (deployed) position in some examples. In particular, the pin 22 can form the eyelet 58 for passage of the suture 16 therethrough and the bullet 26 can be configured to be clear of (i.e. be distally spaced from) the eyelet 58 when the member 34 is in the first position.

According to some examples, the outer body 28 can comprise an expandable shell constructed of polymeric or other material. The wing projections 60 in some cases can be configured to be deformable. In some cases the materials can be resorbable as desired. The expansion of the outer body 28 can be facilitated by the slit 56 along with other structures of the bullet 26 (e.g., the protrusion 42 and the shape and size of the body 40, or the like). Thus, the member 34 can be configured to cause the outer body 28 to expand when the member 34 is in the second position (see e.g., FIG. 4) relative to the first position of FIGS. 3A to 3C.

FIGS. 3C and 3D show cross-sections of the anchoring device 14 and the pin 22 taken along the lines shown in FIG. 3B. FIG. 3C extends through the wing projections 60 while FIG. 3D extends through the troughs 61. FIGS. 3C and 3D are taken in a plane generally orthogonal to the longitudinal axis A. FIGS. 3C and 3D illustrate features of the outer body 28 previously discussed including the wall 46, outer surface 48, the first side 62 and the second side 64. Additionally, FIGS. 3C and 3D illustrate the wall 46 can include a first thickness $T_1$, a second thickness $T_2$, a third side 66, and a fourth side 68. The third side 66 can include a third thickness $T_3$ and the fourth side 68 can include a fourth thickness $T_4$.

As shown in the example of FIGS. 3C and 3D, the body 28 can have the wall 46 with the outer surface 48 thereof configured to engage the bone of a patient. The wall 46 can have the first side 62 having the first thickness $T_1$ in cross-section as measured from the outer surface 48 thereof to the longitudinal axis A. The wall 46 can have the second side 64 having the second thickness $T_2$ in cross-section as measured from the outer surface 48 thereof to the longitudinal axis A. As shown in the example of FIGS. 3C and 3D, the first thickness $T_1$ differs from the second thickness $T_2$. This can be due to the differing size and/or shape of the first side 62 relative to the second side 64. In FIGS. 3C and 3D, the first side 62 can be disposed substantially transverse to the second side 64 and the extent of the first thickness $T_1$ can exceed the extent of the second thickness $T_2$.

In one example, the body 28 can have an irregular cross-sectional profile along the longitudinal axis A from the proximal end 50 (FIGS. 3A and 3B) to the distal end 52 (FIGS. 3A and 3B) of the body 28 such that at least the first side 62 varies in shape with a differing thickness along the longitudinal axis A. Such varying thickness is illustrated, for example, when comparing the extent of the first thickness $T_1$ in FIG. 3C as compared to the extent of the first thickness $T_1$ in FIG. 3D. Thus, wing projections 60 and troughs 61 can provide the first side 62 with a varying shape and with the differing thickness along the longitudinal axis A.

According to further examples, the first side 62 of the wall 46 includes the wing projections 60 and the valleys 61 along at least a part of the outer surface 48 thereof. The wing projections 60 and the valleys 61 can extend along the longitudinal axis A. Similarly, the wall 46 can include at least the third side 66 with one or more wing projections 60 and one or more valleys 61 along at least a second part of the outer surface 48 thereof. As shown in FIG. 3D, the third side 66 can be spaced at an angle from the first side 62 about the longitudinal axis A. According to the example of FIG. 3D, the angle can be substantially 180 degrees (e.g., on the opposing side of the body 46 therefrom). The fourth side 68 can be spaced 180 degrees from the second side 64 (e.g., on the opposing side of the body 46 therefrom) about the longitudinal axis A. As shown in FIG. 3C, a first distance $D_1$ between the outer surface 48 of the second side 64 of the wall 46 and the outer surface 48 of the fourth side 68 of the wall 46 can be less than a second distance $D_2$ between the outer surface 48 of the third side 66 of the wall 46 and the outer surface 48 of the first side 62 of the wall 46. For example, in one case $D_1$ can comprise about 3 mm and $D_2$ can comprise about 5 mm.

Although first side 62 and the second side 66 (and similarly the second side 64 and the fourth side 68) can be configured to share a symmetric shape and similar thicknesses $T_1$ and $T_3$ (and similarly thicknesses $T_2$ and $T_4$ can be similar) as shown in the example of FIGS. 3C and 3D, according to further examples the first side 62 can differ in shape and/or size from the third side 66 such that the thickness $T_1$ can differ from thickness $T_3$. Similarly, according to further examples the second side 64 can differ in shape and/or size from the fourth side 68 such that the thickness $T_2$ can differ from thickness $T_4$. For example, the third side 66 may not include wing projections 60 and troughs 61. Furthermore, according to further examples the wall 46 can be configured with further sides rather than the four illustrated in the example of FIGS. 3C and 3D. For example, the wall 46 could be six sided and could include wing projections and troughs spaced at substantially 120 degrees from one another about the longitudinal axis A.

Figure 4:
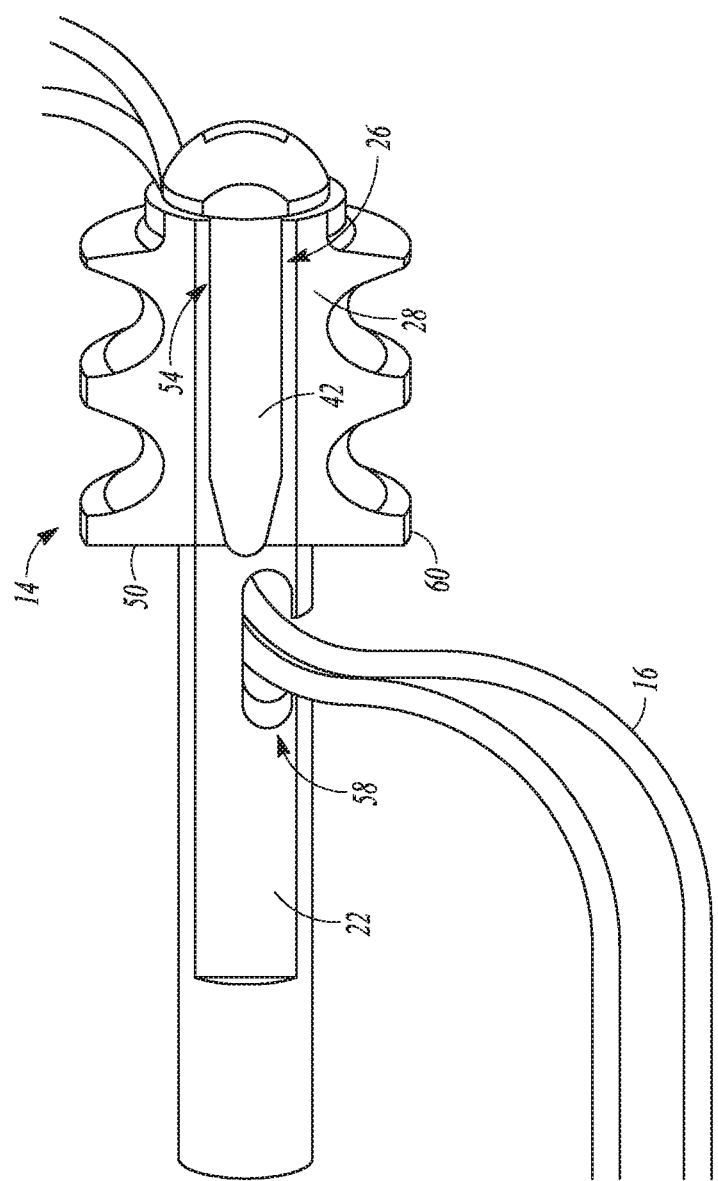
FIG. 4 is a view of the anchoring device from the second perspective employed in FIG. 3B but with the anchoring device in a deployed position in accordance with an example of the present application.

FIG. 4 shows the pin 22 and the anchoring device 14 in the deployed second position. In the second position, the bullet 26 can be pulled into and received within the inner passage 54 of the outer body 28. Together the bullet 26 and the outer body 28 can capture the suture 16 therein and can thereby create a fixation structure for the suture 16 to anchor to. As shown in the deployed position of FIG. 4, the projection 42 can fill the slit 56 in the outer body 28. The pin 22 can be moved proximal of the proximal end portion 50 of the outer body 28. The suture 16 can temporarily remain received in the eyelet 58.

As discussed previously the anchoring device 14 can include an outer expandable outer body and an inner body that can facilitate expansion of the outer body as shown in FIG. 4. A deployment shaft (e.g. the pin 22) can pass through the expandable body and attach to the inner body (e.g., bullet 26). Suture(s) can be passed through the expandable outer body and the deployment shaft. The outer cannula or other portion of the deployment device can be configured to hold the outer body in proximal-distal position beneath the bone surface while the deployment shaft is actuated to deploy the anchor. Actuating the deployment shaft to translate the inner body proximally into the expandable outer body can cause the outer body to expand into bone. The expansion of the outer body can provide for fixation in the bone. The translation of the inner body against the inner wall of the outer body can prevent the suture(s) from moving with respect to the anchor.

Figure 5:
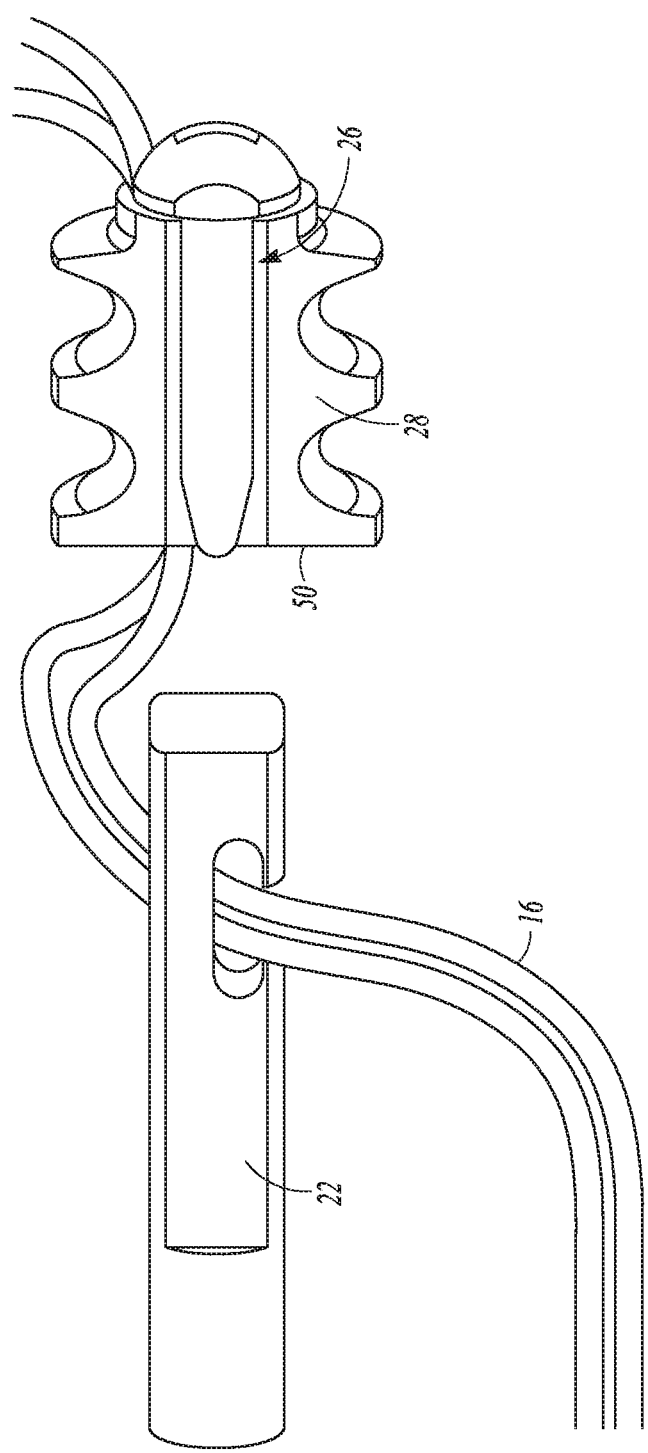
FIG. 5 shows a perspective view of the anchoring device receiving and passing suture therethrough and the deployment tool detached from the anchoring device in accordance with an example of the present application.

As shown in FIG. 5, the anchoring device 14 is now in the deployed position such that the deployment shaft (e.g., pin 22) can be decoupled from the inner body (e.g. bullet 26). The deployment shaft (e.g., the pin 22) can be removed from the outer body 28 and from the patient entirely. Such decoupling can be facilitated by releasing a detent, unscrewing, snapping, breaking the pin 22 or other methods. The suture(s) 16 can be cut after or during translation once they extend from the proximal end portion 50, for example.

Figure 6:
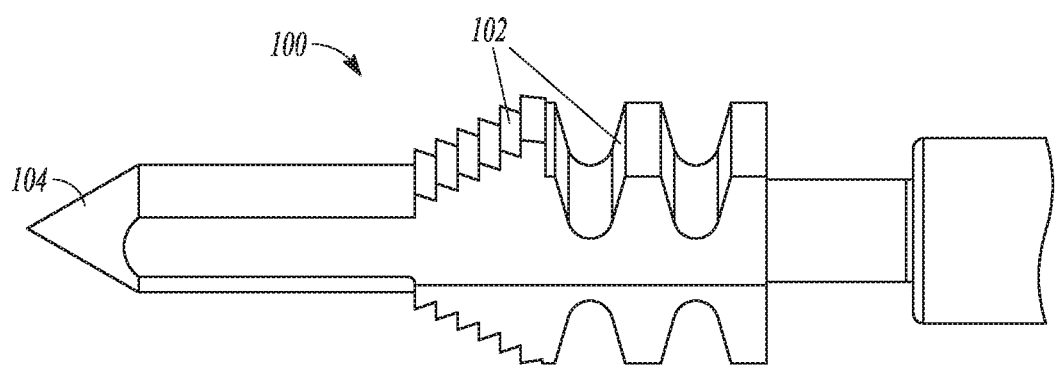
FIG. 6 shows a perspective view of a tapping device in accordance with an example of the present application.

FIG. 6 shows a perspective view of a tapping device 100 according to one example. The tapping device 100 can comprise a cutting device with a plurality of blades 102 and a pointed distal tip 104. The tapping device 100 can be used in the method discussed subsequently in reference to FIGS. 7A to 7D to affix an anchoring device (e.g., the anchoring device 14) into bone.

The blades 102 can have cutting edges configured to cut cancellous bone. Additionally, the tapping device 100 can have a cross-sectional profile configured to substantially match a cross-sectional profile of the outer body 28 (FIGS. 3A and 3B) and the bullet 26 (FIGS. 3A and 3B) with the bullet 26 in the first position as shown in FIGS. 3A and 3B. Thus, the tapping device 100 can have blades shaped to mimic the configuration (e.g., the size and shape) of the wing projections 60 and troughs 61, for example.

FIGS. 7A to 7D show an example of a method 200 that can affix an anchoring device 202 in bone 204. It should be noted the bone contemplated herein can include the cancellous bone of the patient.

Figure 7A:
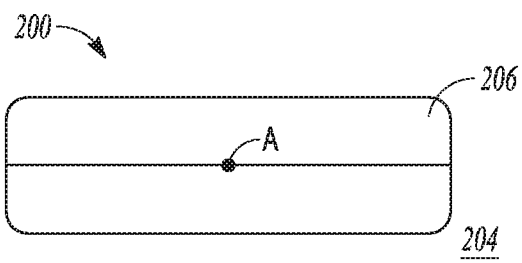
FIGS. 7A to 7D show schematic views of a method of affixing the anchoring device in bone in accordance with an example of the present application.
Figure 7B:
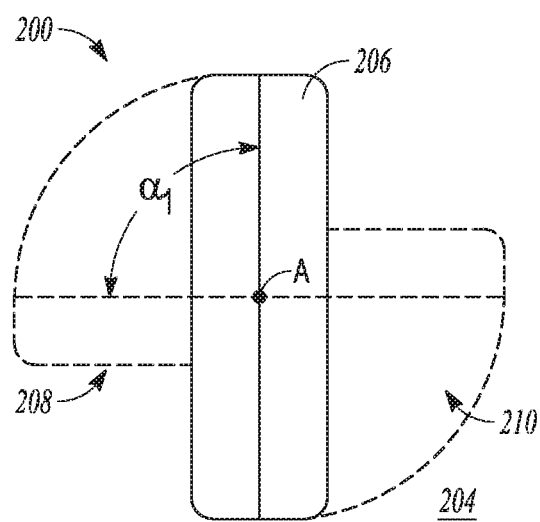

As shown in FIG. 7A, the method 200 can utilize a tapping device 206 that can be constructed in a manner similar to the tapping device 100 previously described in reference to FIG. 6. Both the anchoring device 202 and the tapping device 206 are drawn in a highly schematic manner in FIGS. 7A to 7D for the purposes of illustration of the overall process. As shown in FIG. 7A, the tapping device 206 can be inserted into the bone 204 to create a first recess 208 therein. The first recess 208 can substantially match the outer periphery of the tapping device 206. As shown in FIG. 7B, the tapping device 206 can be rotated about the longitudinal axis A of the tapping device 206 to an angle $\alpha_1$. It should be noted the angle $\alpha_1$ can be any angle. In FIG. 7B, the angle $\alpha_1$ can comprise 90 degrees, which corresponds to a construction of the anchoring device 202. An angle of 90 degrees assumes the construction of the anchoring device 202 can be similar to the construction of the anchoring device 14 previously described and illustrated (e.g., having to opposing surfaces with wing projections 60 and troughs 61). However, if another construction of the anchoring device 202 is utilized the angle $\alpha_1$ can be changed accordingly.

Figure 7C:
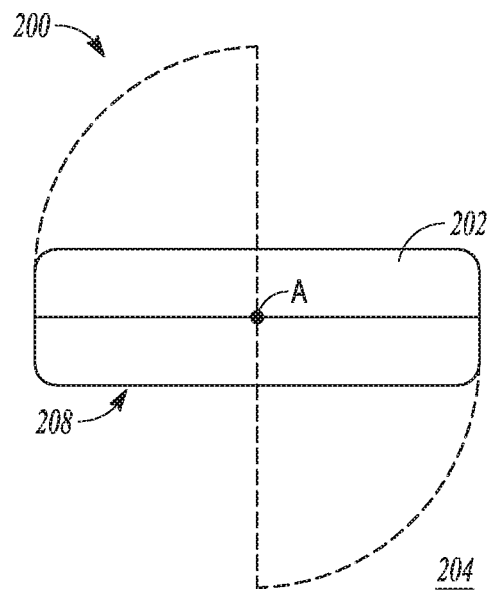

According to the method 200, rotation of the tapping device 206 as shown in FIG. 7B about the longitudinal axis A can create a second recess 210 (illustrated in phantom) in the bone 204. After creation of the second recess 210, the tapping device 206 can be rotated back to its original insertion position (i.e. back into recess 208) of FIG. 7A and removed from the patient. As shown in FIG. 7C, the anchoring device 202 can be inserted into the first recess 208. According to some examples, the anchoring device 202 can be constructed in a manner similar to that of anchoring device 14 as previously described (e.g., the anchoring device 202 can comprise a suture anchor comprising an outer body having a wall with an outer surface configured to engage the bone of a patient and an inner bullet configured to be disposed within the body and moveable along the inner passage relative to the body between a first position and a second position). According to some examples, the wall can have a first side with a first thickness in cross-section and the wall has a second side with a second thickness in cross-section, and the first thickness can differ from the second thickness as previously described and illustrated in reference to FIGS. 3C and 3D. However, according to other examples the anchoring device may be configured in a different manner and may not utilize a two-piece construction (bullet/body) in the manner of the anchoring device 14 described previously.

Figure 7D:
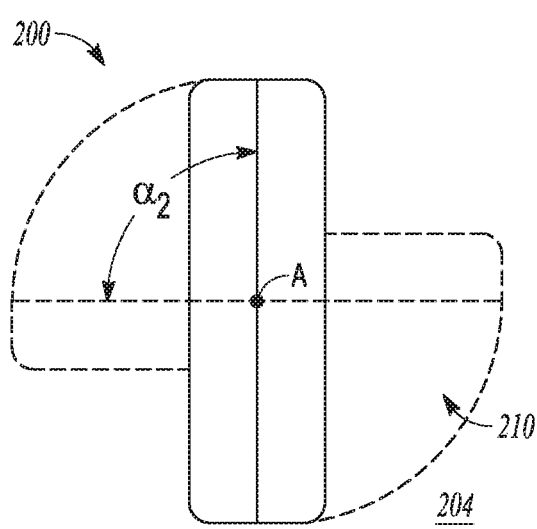

As shown in FIG. 7D, the method 200 can include rotating the anchoring device 202 about the longitudinal axis A of the anchoring device 202 into the second recess 210 (shown in phantom) in the bone 204. Thus, the anchoring device 202 can rotate an angle $\alpha_1$ which can generally correspond to the angle $\alpha_2$ previously created by the tapping device 206. The method 200 can further include actuating movement of the bullet relative to the outer body between the first position and the second position as previously discussed to affix the anchoring device 202 in the bone 204. In some examples, such actuation can cause expansion of the outer body as previously discussed, which can further facilitate affixing of the anchoring device 202 in the bone 204. According to further examples, the method 200 can include an actuation device (e.g., the pin 22) that can be detached from the bullet and can be removed from the body as previously illustrated and described.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A device for anchoring sutured tissue to a bone, the device comprising:
   a body having a wall with an outer surface thereof configured to engage a bone of a patient, the body defining an inner passage extending generally from a proximal end thereof to a distal end thereof, the wall having a rectangular cross-sectional shape so as to have a first side with a first size that differs from a second size of a second side of the wall, wherein the body comprises an expandable shell with deformable wing projections along at least the first side and has a slit formed by the wall thereof along the second side, the slit extending an entirety of a proximal-distal length of the second side of the wall; and
   a member configured to be disposed within the body and moveable along the inner passage relative to the body between a first position and a second position, wherein the member is configured with an eyelet to receive and pass a suture through the member at a position distal of the body when the member is in the first position, wherein the member has a protrusion from an outer surface thereof that generally aligns with the proximal-distal extending slit, the member being configured to facilitate expansion of the body when the member is in the second position relative to the first position, and wherein the eyelet is positioned proximal of the body when the member is in the second position.

2. The device of claim 1, wherein the body has an irregular cross-sectional profile along a longitudinal axis from the proximal end to the distal end of the body such that at least the first side varies in shape with a differing thickness along the longitudinal axis.

3. The device of claim 1, wherein the first side of the wall includes one or more valleys along at least a part of the outer surface thereof, the wing projections and the one or more valleys extending along the longitudinal axis.

4. The device of claim 3, wherein the wall includes at least a third side with deformable wing projections and one or more valleys along at least a second part of the outer surface thereof, the third side spaced at an angle from the first side about the longitudinal axis.

5. The device of claim 3, wherein the wall includes at least a third side with deformable wing projections and one or more valleys along at least a second part of the outer surface thereof, the third side spaced at substantially 180 degrees from the first side about the longitudinal axis.

6. The device of claim 5, wherein the wall includes at least a fourth side spaced 180 degrees from the second side about the longitudinal axis, and wherein a first distance between the outer surface of the second side of the wall and the outer surface of the fourth side of the wall is less than a second distance between the outer surface of the third side of the wall and the outer surface of the first side of the wall.

7. The device of claim 1, wherein the first side has a first thickness in cross-section and the second side having a second thickness in cross-section, and wherein the first thickness differs from the second thickness, and wherein the first side is disposed transverse to the second side and the first thickness exceeds the second thickness.

8. The device of claim 1, wherein the member comprises:
   a bullet having a distal end configured to engage the bone of the patient, the bullet configured to remain within the body; and a deployment pin configured to be detachable from the bullet and removable from the body, wherein the deployment pin is actuatable relative to the body to move the bullet to the second position relative to the body and thereby form a deployed configuration of the device.

9. The device of claim 8, wherein the deployment pin forms the eyelet and the deployment pin is configured to pull the suture through the inner passage and out of the proximal end of the body.

10. The system of claim 1, wherein the member is configured with a first portion and a second portion, wherein in the second position the first portion is configured to be detachable from the second portion and is removable from the body leaving the second portion positioned within the body.

11. A system for anchoring a sutured tissue to a bone, the system comprising:
one or more sutures;
an outer body having a wall with an outer surface configured to engage a bone of a patient, the body having an inner passage extending generally from a proximal end thereof to a distal end thereof, the wall having a rectangular cross-sectional shape so as to have a first side with a first size that differs from a second size of a second side of the wall, wherein the body comprises an expandable shell and has a slit formed by the wall thereof along the second side, the slit extending an entirety of a proximal-distal length of the second side of the wall;
an inner bullet configured to be disposed within the body and moveable along the inner passage relative to the body from a first position to a second position, wherein the bullet has a protrusion from an outer surface thereof that generally aligns with the proximal-distal extending slit, the bullet being configured to facilitate expansion of the body when the bullet is in the second position relative to the first position; and
a surgical tool configured to actuate movement of the bullet relative to the body between the first position and the second position via a deployment pin that is coupleable to the bullet, wherein in the first position the deployment pin extends through the body via the inner passage and has an eyelet configured to capture the one or more sutures distal of the body, and wherein in the second position the deployment pin is configured to be detachable from the bullet and removable from the body leaving the bullet positioned within the body and the one or more sutures captured between the bullet and the body.

12. The system of claim 11, wherein the body has an irregular cross-sectional profile along a longitudinal axis from the proximal end to the distal end of the body such that at least a first thickness of a first side of the wall varies along the longitudinal axis.

13. The system of claim 11, wherein the wall has a first side with a first thickness in cross-section and the wall has a second side with a second thickness in cross-section, and wherein the first thickness differs from the second thickness.

14. The system of claim 13, wherein the first side of the wall includes one or more projections and one or more valleys along at least a part of the outer surface thereof, the one or more projections and the one or more valleys extending along a longitudinal axis of the body.

15. The system of claim 13, wherein the wall includes at least a third side with one or more projections and one or more valleys along at least a second part of the outer surface thereof, the third side spaced at an angle from the first side about a longitudinal axis of the body.

16. The system of claim 13, wherein the wall includes at least a third side spaced 180 degrees from the first side about a longitudinal axis and a fourth side spaced 180 degrees from the second side about the longitudinal axis, and wherein a first distance between the outer surface of the second side of the wall and the outer surface of the fourth side of the wall is less than a second distance between the outer surface of a third side of the wall and the outer surface of the fourth side of the wall.

17. The system of claim 11, further comprising a tap tool having one or more cutting edges configured to cut cancellous bone, the tap tool having a cross-sectional profile configured to substantially match a cross-sectional profile of the body and the bullet with the bullet in the first position.

18. The system of claim 11, wherein the eyelet is configured to capture the one or more sutures in the second position at a position proximal of the body and bullet.

* * * * *